United States Patent [19]

Dattagupta et al.

[11] Patent Number: 5,026,840

[45] Date of Patent: * Jun. 25, 1991

[54] PHOTOCHEMICAL NUCLEIC ACID-LABELING REAGENT HAVING A POLYALKLAMINE SPACER

[75] Inventors: Nanibhushan Dattagupta, New Haven, Conn.; James P. Albarella, Elkhart, Ind.

[73] Assignee: Molecular Diagnostics, Inc., West Haven, Conn.

[*] Notice: The portion of the term of this patent subsequent to Aug. 21, 2007 has been disclaimed.

[21] Appl. No.: 475,639

[22] Filed: Feb. 6, 1990

Related U.S. Application Data

[63] Continuation of Ser. No. 27,384, Mar. 18, 1987, Pat. No. 4,950,744, which is a continuation-in-part of Ser. No. 690,336, Jan. 10, 1985, abandoned.

[51] Int. Cl.$^5$ .................. C07H 15/12; C12Q 1/00
[52] U.S. Cl. .................. 536/27; 435/4; 435/6; 435/188; 436/63; 436/94; 436/501
[58] Field of Search .............. 536/27; 435/4, 6, 188; 436/63, 94, 501

[56] References Cited

U.S. PATENT DOCUMENTS

| | | | |
|---|---|---|---|
| 4,582,789 | 4/1986 | Sheldon et al. | 435/6 |
| 4,599,303 | 7/1986 | Yabusaki et al. | 435/6 |
| 4,617,261 | 11/1986 | Sheldon, III et al. | 435/6 |
| 4,737,454 | 4/1988 | Dattagupta et al. | 435/6 |

FOREIGN PATENT DOCUMENTS

| | | |
|---|---|---|
| 4200 | 3/1984 | Australia . |
| 7500 | 10/1984 | Australia . |
| 40310 | 10/1985 | Australia . |
| 0124221 | 11/1984 | European Pat. Off. . |
| 0130515 | 1/1985 | European Pat. Off. . |
| 0131830 | 1/1985 | European Pat. Off. . |
| 0138357 | 4/1985 | European Pat. Off. . |
| 0156287 | 10/1985 | European Pat. Off. . |
| 8502628 | 6/1985 | PCT Int'l Appl. . |

OTHER PUBLICATIONS

Lown et al, "Bis-intercalative Binding to DNA of Novel bis(10-methyl)acridinium Chlorides and Its Dependence on Chain Length of Linker", *Can. J. Biochem. 1978, 56(11), 1006–1015.*

Hansen et al, "Acridine-psoralen Amines and Their Interaction with DNA", *Biochemistry*, 22(21), 4878–4886, 1983.

*Primary Examiner*—John W. Rollins
*Attorney, Agent, or Firm*—Sprung Horn Kramer & Woods

[57] ABSTRACT

A photochemical nucleic acid-labeling reagent of the formula

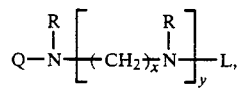

wherein Q is a photoreactive residue of a nucleic acid-binding ligand; L is a detectable label residue; R is hydrogen, $C_1$ to $C_7$-alkyl, aryl, hydroxy, or $C_1$ to $C_7$-alkoxy; x is an integer from 2 through 7; and Y is an integer from 3 through 10; wherein R and x, respectively, can be the same or different each time they appear in the formula. The reagent is useful in the highly efficient labeling of nucleic acids for the purpose of detection in hybridization assays.

25 Claims, No Drawings

PHOTOCHEMICAL NUCLEIC ACID-LABELING REAGENT HAVING A POLYALKLAMINE SPACER

CROSS-REFERENCE TO RELATED APPLICATION

This is a continuation, of application Ser. No. 07/027,384, filed Mar. 18, 1987, now U.S. Pat. No. 4,950,244, which is a continuation-in-part application of application Ser. No. 690,336, filed Jan. 10, 1985, now abandoned.

BACKGROUND OF THE INVENTION

1. Field of the Invention

This application relates to the provision of labeled nucleic acids suitable for hybridization assays.

2. Background Information

In application Ser. No. 611,668, filed May 18, 1984, now U.S. Pat. No. 4,787,454, there is described a photochemical method of labelling nucleic acids for detection purposes in hybridization assays for the determination of specific polynucleotide sequences. The assays are of the type described in application Ser. No. 815,694, filed Jan. 2, 1986, now abandoned.

The labeled probes of application Ser. No. 661,668 comprise (a) a nucleic acid component, (b) a nucleic acid-binding ligand photochemically linked to the nucleic acid component, and (c) a label chemically linked to (b). These probes generally perform quite satisfactorily, but in some instances it is desirable to improve their performance.

SUMMARY OF THE INVENTION

It is an object of the present invention to provide a labeled nucleic acid of improved solubility, to increase the efficiency of preparing such molecules which is important when the test sample is being labeled, and to improve the sensitivity of the probe in an assay.

These and other objects and advantages are realized in accordance with the present invention pursuant to which there is provided a photochemical nucleic-acid labeling reagent of the formula

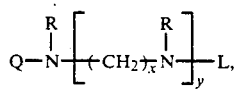

wherein Q is a photoreactive residue of a nucleic acid-binding ligand; L is a detectable label residue; R is hydrogen, $C_1$ to $C_7$-alkyl, aryl (e.g., phenyl, naphthyl and anthracyl), hydroxy, or $C_1$ to $C_7$-alkoxy; x is an integer from 2 to 7; y is an integer from 3 to 10; wherein R and x, respectively, can be the same or different each time they appear in the formula.

The present invention also concerns a labeled nucleic acid comprising (a) a nucleic acid component, (b) a nucleic acid-binding ligand photochemically linked to the nucleic acid component, (c) a label and (d) a polyalkylamine spacer chemically linking (b) and (c), such as a residue of spermine.

BRIEF DESCRIPTION OF THE DRAWING

The Figure is a photograph of immobilized cell lysates that have not been photochemically labeled for comparison purposes with compounds of the present invention and compounds of the prior art.

DETAILED DESCRIPTION OF THE INVENTION

The spacer of the present invention is a polyalkylamine residue of the formula

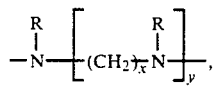

wherein R is hydrogen, $C_1$ to $C_7$-alkyl, aryl (e.g., phenyl, naphthyl and anthracyl), hydroxy, or $C_1$ to $C_7$-alkoxy; x is an integer from 2 through 7; and y is an integer from 3 through 10. R and x, respectively, can be the same or different each time they appear in the spacer residue, that is, the R groups that appear along the spacer residue do not have to be identical, e.g., one or more can be hydrogen, one or more can be alkyl, one or more can be hydroxyl, and so forth, and the alkylene groups —($CH_2$)— do not have to be of the same length along the spacer residue, e.g., the first may be propylene, the second butylene, the third propylene, and so forth. Generally, the R and alkylene groups can vary independently of their position on the spacer residue.

Preferably, the R groups are independently selected from hydrogen and $C_1$ to $C_4$-alkyl, e.g., methyl, ethyl, n-propyl, iso-propyl, n-butyl, iso-butyl, tert-butyl; x is, independently, an integer from 2 through 5; and y is an integer from 3 through 6. A particularly useful spacer residue is the residue of N-4, N-9-dimethylspermine having the formula

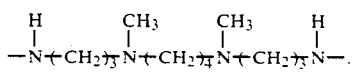

The spacer can be incorporated at any stage of the process of making the labeled nucleic acid a—b—d—c defined hereinabove. Thus the sequence can be any of the following:

a+b+d+c, b+d+c+a, d+c+b+a, b+d+a+c, etc.

The conditions for the individual steps are well known in chemistry.

As set forth in application Ser. No. 611,668, supra, the nucleic acid is joined to the ligand photochemically, employing a photoreactive nucleic acid-binding ligand, e.g., an intercalator compound such as a furocoumarin, a phenanthridine, an anthracycline, a phenazine, an acridine, a phenothiazine, a quinoline, or a non-intercalator compound such as netropsin, distamycin, Hoechst 33258 or bis-benzimidazole to link the nucleic acid to a label which can be "read" or assayed in a conventional manner, including fluorescence detection. The end product is thus a labeled nucleic acid comprising (a) a nucleic acid component, (b) an intercalator or other nucleic acid-binding ligand photochemically linked to the nucleic acid component, and (c) a label chemically linked to (b) through the spacer residue of the present invention.

The nucleic acid can be DNA, RNA, an oligonucleotide or a probe such as described in application Ser. No. 815,694, described supra, from higher eukaryotes such as humans and other animals, procaryotes such as plants, fungi, bacteria, viruses, and the like, yeasts, etc. The nucleic acid can be of known composition or can be unknown, as in a sample to be assayed, e.g., a known unlabeled probe is immobilized and thereafter subjected to hybridization conditions with an unknown nucleic acid sample labeled in accordance with the invention.

The novel photochemical method provides more favorable reaction conditions than the usual chemical coupling method for biochemically sensitive substances. By using proper wavelengths for irradiation, DNA, RNA and oligonucleotides can be modified without affecting the native structure of the polymers. The nucleic acid-binding ligand, hereinafter exemplified by an intercalator, and label can first be coupled and then photoreacted with the nucleic acid or the nucleic acid can first be photoreacted with the intercalator and then coupled to the label. A general scheme for coupling a nucleic acid, exemplified by double-stranded DNA, to a label such as a hapten or enzyme is as follows:

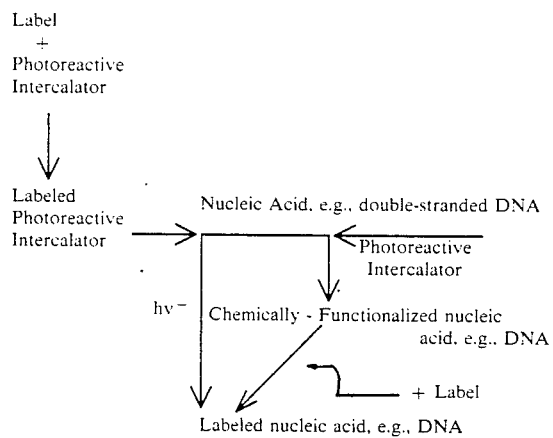

Where the hybridizable portion of the probe is in a double stranded form, such portion is then denatured to yield a hybridizable single stranded portion. Alternatively, where the labeled nucleic acid, e.g., DNA, comprises the hybridizable portion already in single stranded form, such denaturization can be avoided if desired. Alternatively, nucleic acid, e.g., double stranded DNA, can be labeled by the approach of the present invention after hybridization has occurred using a hybridization format which generates nucleic acid, e.g., double stranded DNA, only in the presence of the sequence to be detected.

To produce specific and efficient photochemical products, it is desirable that the nucleic acid component and the photoreactive intercalator compound be allowed to react in the dark in a specific manner.

For coupling to nucleic acid, e.g., DNA, aminomethyl psoralen, aminomethyl angelicin and amino alkyl ethidium or methidium azides are particularly useful compounds. They bind to double-stranded DNA and only the complex produces a photoadduct. In the case where labeled double-stranded DNA must be denatured in order to yield a hybridizable single stranded region, conditions are employed so that simultaneous interaction of two strands of DNA with a single photoadduct is prevented. It is necessary that the frequency of modification along a hybridizable single stranded portion of the probe not be so great as to substantially prevent hybridization, and accordingly there preferably will be not more than one site of modification per 25, more usually 50, and preferably 100, nucleotide bases.

Suitable angelicin derivatives have the following formula

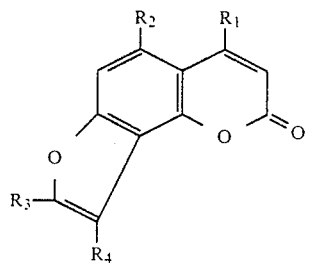

in which $R^1$, $R^2$ and $R^3$ each independently is hydrogen or $C_1$-$C_7$-alkyl; and $R^4$ is hydrogen, $C_1$-$C_7$-alkyl or lower alkyl substituted with hydroxy, $C_1$-$C_7$-alkoxy, amino, halo, or

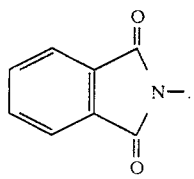

Particularly preferred angelicin derivatives have the following moieties for $R_1$, $R_2$, $R_3$ and $R_4$:

| $R_1$ | $R_2$ | $R_3$ | $R_4$ |
|---|---|---|---|
| H | H | H | H |
| $CH_3$ | H | $CH_3$ | H |
| $CH_3$ | $CH_3$ | $CH_3$ | $CH_2OH$ |
| $CH_3$ | H | $CH_3$ | $CH_2OCH_3$ |
| $CH_3$ | H | $CH_3$ | $CH_2NH_2$ |
| H | H | $CH_3$ | $CH_2Cl$ |
| H | H | $CH_3$ | 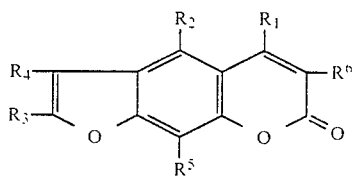 |

Many other compounds with different R's can be synthesized following published procedures.

Suitable psoralen derivatives have the formula

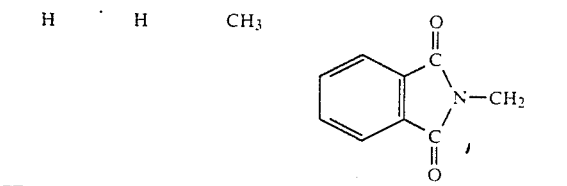

in which $R_1$, $R_3$ and $R_6$ each independently is hydrogen or lower alkyl, $R_4$ is hydrogen, $C_1$–$C_7$-alkyl or $C_1$–$C_7$-alkyl substituted by hydroxy, $C_1$–$C_7$-alkoxy, amino, halo or

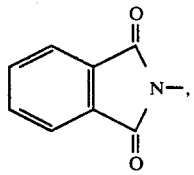

and $R_2$ and $R_5$ each independently is hydrogen, hydroxy, carboxy, carbo-$C_1$–$C_7$-alkoxy or $C_1$–$C_7$-alkoxy.

Angelicin derivatives are superior to psoralen compounds for monoadduct formation. If a single-stranded probe is covalently attached to some extra double-stranded nucleic acid, e.g., DNA, use of phenanthridium and psoralen compounds is desirable since these compounds interact specifically to double-stranded nucleic acid, e.g., DNA, in the dark. The chemistry for the synthesis of the coupled reagents to modify nucleic acids for labeling, described more fully hereinbelow, is similar for all cases.

The nucleic acid component can be singly or doubly stranded DNA or RNA or fragments thereof such as are produced by restriction enzymes or even relatively short oligomers.

The nucleic acid-binding ligands of the present invention used to link the nucleic acid component to the label can be any suitable photoreactive form of known nucleic acid-binding ligands. Particularly preferred nucleic acid-binding ligands are intercalator compounds such as the furocoumarins, e.g., angelicin (isopsoralen) or psoralen or derivatives thereof which photochemically will react with nucleic acids, e.g., 4'-aminomethyl-4,5'-dimethyl angelicin, 4'-aminomethyl-trioxsalen (4'-aminomethyl-4,5',8-trimethyl-psoralen), 3-carboxy-5-aminopsoralen, 3-carboxy-8-aminopsoralen, 3-carboxy-8-hydroxypsoralen, and 4,5'-dimethyl-8-methoxy psoralen, as well as the phenanthridines, e.g., the mono- or bis-azido amino-alkyl methidium or ethidium compounds. Photoreactive forms of a variety of other intercalating agents can generally be used as exemplified in the following table:

| Intercalator Classes and Representative Compounds | Literature References |
|---|---|
| A. Acridine dyes proflavin, acridine orange, quinacrine, acriflavine | Lerman, J. Mol. Biol. 3:18 (1961); Bloomfield et al, "Physical Chemistry of Nucleic Acids", Chapter 7, pp. 429–476, Harper and Rowe, NY (1974) Miller et al, Biopolymers 19:2091 (1980) |
| B. Phenanthridines ethidium coralyne ellipticine, ellipticine cation and derivatives | Bloomfield et al, supra Miller et al, supra Wilson et al, J. Med. Chem. 19:1261 (1976) Fety et al, FEBS Letters 17:321 (1971); Kohn et al, Cancer Res. 35:71 (1976); LePecq et al, PNAS (USA) 71: 5078 (1974); Pelaprat et al, J. Med. Chem. 23:1330 (1980) |
| C. Phenazines | Bloomfield et al, supra |
| 5-methylphenazine cation | |
| D. Phenothiazines chlopromazine | " |
| E. Quinolines chloroquine quinine | " |
| F. Aflatoxin | " |
| G. Polycyclic hydrocarbons and their oxirane derivatives | " |
| 3,4-benzpyrene benzopyrene diol epoxidie, 1-pyrenyl-oxirane | Yange et al, Biochem. Biophys. Res. Comm. 82:929 (1978) |
| benzanthracene-5,6-oxide | Amea et al, Science 176:47 (1972) |
| H. Actinomycins actinomycin D | Bloomfield et al, supra |
| I. Anthracyclinones beta-rhodomycin A daunamycin | " |
| J. Thiaxanthenones miracil D | " |
| K. Anthramycin | " |
| L. Mitomycin | Ogawa et al, Nucl. Acids Res., Spec. Publ. 3:79 (1977) Akhtar et al, Can. J. Chem. 53:2891 (1975) |
| M. Platinium Complexes | Lippard, Accts. Chem. Res. 11:211 (1978) |
| N. Polyintercalators | |
| echinomycin | Waring et al, Nature 252:653 (1974); Wakelin, Biochem. J. 157:721 (1976) |
| quinomycin triostin BBM928A tandem | Lee et al, Biochem. J. 173:115 (1978); Huang et al, Biochem. 19: 5537 (1980); Viswamitra et al, Nature 289: 817 (1981) |
| diacridines | LePecq et al, PNAS (USA) 72:2915 (1975); Carrellakis et al, Biochim. Biophys. Acta 418:277 (1976); Wakelin et al, Biochem 17:5057 (1978); Wakelin et al, FEBS Lett. 104:261 (1979); Capelle et al, Biochem. 18:3354 (1979); Wright et al, Biochem; 19:5825 (1980); Bernier et al, Biochem. J. 199:479 (1981); King et al, Biochem. 21:4982 (1982) |
| ethidium dimer | Gaugain et al, Biochem. 17:5078 (1978); Kuhlman et al, Nucl. Acids Res. 5:2629 (1978); Marlcovits et al, Anal. Biochem. 94:259 (1979); Dervan et al, JACS 100: 1968 (1978); Dervan et al, JACS 101:3664 (1979). |
| ellipticene dimers and analogs | Debarre et al, Compt. Rend. Ser. D. 284: 81 (1977); Pelaprat et al, J. Med. Chem. 23:1336 (1980) |
| heterodimers | Cain et al, J. Med. Chem. 21:658 (1978); Gaugain et al, Biochem. 17:5078 (1978) |
| trimers | Hansen et al, JCS Chem. Comm. 162 (1983); Atnell et al, JACS |

| Intercalator Classes and Representative Compounds | Literature References |
| --- | --- |
| | 105:2913 (1983) |
| O. Norphillin A | Loun et al, JACS 104: 3213 (1982) |
| P. Fluorenes and fluorenones fluorenodiamines | Bloomfield et al, supra Witkowski et al, Wiss. Beitr.-Martin-Luther-Univ. Halle Wittenberg, 11 (1981) |
| Q. Furocoumarins | |
| angelicin | Venema et al, MGG, Mol. Gen. Genet. 179;1 (1980) |
| 4,5'-dimethylangelicin | Vedaldi et al, Chem.-Biol. Interact. 36: 275 (1981) |
| psoralen | Marciani et al, Z. Naturforsch B 27 (2): 196 (1972) |
| 8-methoxypsoralen | Belognzov et al, Mutat. Res. 84:11 (1981); Scott et al, Photochem. Photobiol. 34:63 (1981) |
| 5-aminomethyl-8-methoxypsoralen | Hansen et al, Tet. Lett. 22:1847 (1981) |
| 4,5,8-trimethylpsoralen | Ben-Hur et al, Biochem. Biophys. Acta 331:181 (1973) |
| 4'-aminomethyl-4,5,8-trimethylpsoralen | Issacs et al, Biochem. 16:1058 (1977) |
| xanthotoxin | Hradecma et al, Acta Virol. (Engl. Ed.) 26: 305 (1982) |
| khellin | Beaumont et al, Biochim. Biophys. Acta 608:1829 (1980) |
| R. Benzodipyrones | Murx et al. J. Het. Chem. 12:417 (1975); Horter et al, Photochem. Photobiol. 20: 407 (1974) |
| S. Monostral Fast Blue | Juarranz et al, Acta Histochem. 70:130 (1982) |

Particularly useful photoreactive forms of such intercalating agents are the azidointercalators. Their reactive nitrenes are readily generated at long wavelength ultraviolet or visible light and the nitrenes of arylazides prefer insertion reactions over their rearrangement products [see White et al, *Methods in Enzymol.*, 46, 644, (1977)]. Representative azidointercalators are 3-azidoacridine, 9-azidoacridine, ethidium monoazide, ethidium diazide, ethidium dimer azide [Mitchell et al, JACS, 104, 4265, (1982)], 4-azido-7-chloroquinoline, and 2-azidofluorene. Other useful photoreactable intercalators are the furocoumarins which form [2+2] cycloadducts with pyrimidine residues. Alkylating agents can also be used such as bischloroethylamines and epoxides or aziridines, e.g., aflatoxins, polycyclic hydrocarbon epoxides, mitomycin, and norphillin A.

The label which is linked to the nucleic acid component according to the present invention can be any chemical group or residue having a detectable physical or chemical property. The label will bear a functional chemical group to enable it to be chemically linked to the intercalator compound. Such labeling materials have been well developed in the field of immunoassays and in general most any label useful in such methods can be applied to the present invention. Particularly useful are enzymatically active groups, such as enzymes (see *Clin. Chem.*, (1976), 22, 1243), enzyme substrates (see British Pat. Spec. 1,548,741), coenzymes (see U.S. Pat. Nos. 4,230,797 and 4,238,565), and enzyme inhibitors (see U.S. Pat. No. 4,134,792; fluorescers (see *Clin. Chem.*, (1979), 25, 353) and chromophores including phycobiliproteins; luminescers such as chemiluminescers and bioluminescers (see *Clin. Chem.*, (1979), 25, 512, and ibid, 1531); specifically bindable ligands; and residues comprising radioisotopes such as $^3H$, $^{35}S$, $^{32}P$, $^{125}I$, and $^{14}C$. Such labels are detected on the basis of their own physical properties (e.g., fluorescers, chromophores and radioisotopes) or their reactive or binding properties (e.g., enzymes, substrates, coenzymes and inhibitors). For example, a cofactor-labeled nucleic acid can be detected by adding the enzyme for which the label is a cofactor and a substrate for the enzyme. A hapten or ligand (e.g., biotin) labeled nucleic acid can be detected by adding an antibody or an antibody fragment to the hapten or a protein (e.g., avidin) which binds the ligand, tagged with a detectable molecule. Such detectable molecule can be some molecule with a measurable physical property (e.g., fluorescence or absorbance) or a participant in an enzyme reaction (e.g., see above list). For example, one can use an enzyme which acts upon a substrate to generate a product with a measurable physical property. Examples of the latter include, but are not limited to, beta-galactosidase, alkaline phosphatase, papain, and peroxidase. For in situ hybridization studies, ideally the final product is water insoluble. Other labels will be evident to one of the ordinary skill in the art.

The particular sequence in making the labeled nucleic acid can be varied. Thus, for example, an amino-substituted psoralen can first be photometrically coupled with a nucleic acid, the product having pendant amino groups by which it can be coupled to the label. Alternatively, the psoralen can first be coupled to a label such as an enzyme and then to the nucleic acid.

The spacer chain length between the nucleic acid-binding ligand and the label can be extended via hydrocarbon or peptide. A typical example involves extending an 8-hydroxy psoralen derivative with an alkyl halide, according to the method described by J. L. DeCout and J. Lhomme, *Photochemistry Photobiology*, 37, 155–161 (1983). The haloalkylated derivative is then reacted either with thiol or amines to produce the reactive residue, as has been described by W. A. Saffran et al., *Proc. Natl. Acad. Sci., U.S.A.*, 79, 4594 (1982).

If the label is an enzyme, for example, the product will ultimately be placed on a suitable medium and the extent of catalysis will be determined. Thus, if the enzyme is a phosphatase the medium could contain nitrophenyl phosphate and one would monitor the amount of nitrophenol generated by observing the color. If the enzyme is a beta-galactosidase the medium can contain o-nitrophenyl-D-galacto-pyranoside which also will liberate nitrophenol.

The labeled nucleic acid of the present invention is applicable to all conventional hybridization assay formats, and in general to any format that is possible based on formation a hybridization product or aggregate comprising the labeled nucleic acid. In particular, the unique labeled probe of the present invention can be used in solution and solid-phase hybridization formats, including, in the latter case, formats involving immobilization of either sample or probe nucleic acids and sandwich formats.

The labeled nucleic acid probe will comprise at least one single stranded base sequence substantially complementary to or homologous with the sequence to be detected. However, such base sequence need not be a single continuous polynucleotide segment, but can be comprised of two or more individual segments interrupted by nonhomologous sequences. These nonhomologous sequences can be linear or they can be self-complementary and form hairpin loops. In addition, the homologous region of the probe can be flanked at the 3'- and 5'-terminii by nonhomologous sequences, such as those comprising the DNA or RNA of a vector into which the homologous sequence had been inserted for propagation. In either instance, the probe as presented as an analytical reagent will exhibit detectable hybridization at one or more points with sample nucleic acids of interest. Linear or circular single stranded polynucleotides can be used as the probe element, with major or minor portions being duplexed with a complementary polynucleotide strand or strands, provided that the critical homologous segment or segments are in single stranded form and available for hybridization with sample DNA or RNA. Useful probes include linear or circular probes wherein the homologous probe sequence is in essentially only single stranded form [see particularly, Hu and Messing, *Gene*, 17, 271, (1982)].

The labeled probe of the present invention can be used in any conventional hybridization technique. As improvements are made and as conceptually new formats are developed, such can be readily applied to the present labeled probe. Conventional hybridization formats which are particularly useful include those wherein the sample nucleic acids or the polynucleotide probe is immobilized on a solid support (solid-phase hybridization) and those wherein the polynucleotide species are all in solution (solution hybridization).

In solid-phase hybridization formats, one of the polynucleotide species participating in hybridization is fixed in an appropriate manner in its single stranded form to a solid support. Useful solid supports are well known in the art and include those which bind nucleic acids either covalently or non-covalently. Noncovalent supports which are generally understood to involve hydrophobic bonding include naturally occurring and synthetic polymeric materials, such as nitrocellulose, derivatized nylon, and fluorinated polyhydrocarbons, in a variety of forms such as filters or solid sheets. Covalent binding supports are also useful and comprise materials having chemically reactive groups or groups, such as dichlorotriazine, diazobenzyloxymethyl, and the like, which can be activated for binding to polynucleotides.

A typical solid-phase hybridization technique begins with immobilization of sample nucleic acids onto the support in single stranded form. This initial step essentially prevents reannealing of complementary strands from the sample and can be used as a means for concentrating sample material on the support for enhanced detectability. The polynucleotide probe is then contacted with the support and hybridization detected by measurement of the label as described herein. The solid support provides a convenient means for separating labeled probe which has hybridized to the sequence to be detected from that which has not hybridized.

Another method of interest is the sandwich hybridization technique wherein one of two mutually exclusive fragments of the homologous sequence of the probe is immobilized and the other is labelled. The presence of the polynucleotide sequence of interest results in dual hybridization to the immobilized and labeled probe segments. See *Methods in Enzymology* 65, 468, (1980) and *Gene* 21, 77–85, (1983) for further details.

The present invention will now be described with reference to the following non-limiting examples.

EXAMPLES

All preparations involving either azidophenyl or furocoumarin derivatives were handled in a darkroom under safelight conditions.

Infrared (IR) spectra were obtained with a Perkin-Elmer Model 710B or 237 infrared spectrophotometer, or on a Nicolet 5DBXB FT IR spectrometer, unless otherwise noted. A 1602 cm$^{-1}$ band of polystyrene film was used as an external calibration standard. Signals were reported as cm$^{-1}$.

Proton magnetic resonance ($^1$H NMR) spectra were obtained at 89.55 MHz using a JEOL FX-900 spectrometer or at 60 MHz using a Varian T-60 spectrometer; spectra were obtained in CDCl$_3$ solution, unless otherwise noted. Chemical shifts were reported in parts per million downfield from the internal standard tetramethylsilane.

Mass spectra (MS) were obtained on a Hewlett-Packard 5985A spectrometer operating in either an electron impact (EI), chemical ionization (CI), or fast atom bombardment (FAB) mode.

Organic reagents were obtained from Aldrich Chemical Company and were used without purification, unless otherwise noted. Inorganic reagents were ACS reagant grade from Fisher Scientific Company or any other major vendor. Reaction solvents were ACS reagent grade; tetrahydrofuran (THF) was HPLC grade from J. T. Baker Chemical Company. Brine refers to a saturated aqueous sodium chloride solution.

Thin layer chromatograph (TCL) was performed using silica gel 60F-254 plates from E. Merck. Flash column chromatography was performed using E. Merck or American Scientific Products Silica Gel 60 (230–400 mesh). All melting points and boiling points reported were uncorrected.

EXAMPLE 1

1-Amino-17-N-(Biotinylamido)-3,6,9,12,15-Pentaoxaheptadecane

A solution containing 7.2 g of 1,17-diamino-3,6,9,12,15-pentaoxaheptadecane, prepared according to Kern et al, *Makromol. Chem.*, 150 (10): 2539, (1979), (25 mmol) in 75 mL of DMF under an argon atmosphere was treated with 3.41 g of N-oxysuccinimidyl biotin (10 mmol) added in portions over 1.0 hour. The resulting solution was stirred for 4 hours at ambient temperature. TLC (SiO$_2$, 70:10:1 CHCl$_3$—CH$_3$OH—concentrated NH$_4$OH) visualized by dimethylaminocinnamaldehyde spray reagent showed excellent conversion to a new product (Rf=0.18). The reaction mixture was divided in half and each half was absorbed onto SiO$_2$ and flash-chromatographed on 500 g of SiO$_2$–60 (230–400 mesh) using a 70:10:1 CHCl$_3$—CH$_3$OH-concentrated NH$_4$OH solvent mixture. Fractions containing the product were pooled and concentrated to give 2.42 g of a gelatinous, waxy solid. The product was precipitated as a solid from isopropanol-ether, washed with hexane, and dried at 55° C. (0.1 mm) to give 1.761 g of a white powder (35% yield).

Analysis: Calculated for C$_{22}$H$_{42}$N$_4$O$_7$S.3/2 H$_2$O: C, 49.51; H, 8.50; N, 10.49; Found: C, 49.59; H, 8.13; N, 10.39.

$^1$H NMR (90 MHz, dmso-d$_6$) δ:1.1–1.7 (m, 6H); 2.05 (t, J=7 Hz, 2H); 2.62 (t, J=4 Hz, 1H); 2.74 (t, J=4 Hz, 1H); 3.0–3.4 (m, 14H); 3.50 (s, 14H); 4.14 (m, 1H); 4.30 (m, 1H); 6.35 (d, J=4 Hz, 1H); 7.80 (m, 1H).

$^{13}$C NMR (22.5 MHz, dmso-d$_6$) δ: 25.2, 28.0, 28.2, 35.1, 40.6, 55.3, 59.2, 61.1, 69.6, 69.8, 71.3, 162.7, 172.1.

IR (KBr) cm$^{-1}$: 2900, 2850, 1690, 1640, 1580, 1540, 1450, 1100.

Mass Spectrum (FAB) m/e: 507.3 (M+1, 56%).

EXAMPLE 2

4'-(Biotinyl-PEG)-4,5'-Dimethylangelicin (Biotinyl-Peg-Angelicin)

EXAMPLE 2A

Small Scale Procedure

A solution of 203 mg of 1-amino-17N-(biotinylamido)-3,6,9,12,15-pentaoxaheptadecane (0.4 mmol) in 1 mL of DMF under an argon atmosphere was treated with 78 mg of N,N-carbonyldimidazole (0.48 mmol). The resulting mixture was stirred for 4 hours and was then treated with 55 mg of 4'-aminomethyl-4,5'-dimethylangelicin hydrochloride (Dall'Acqua et al, J. Med. Chem., 24, 178, (1981)) (0.2 mmol), 140 μL of diisopropylethylamine and 100 μL of DMF. The resulting mixture was stirred overnight at 50° C. The mixture was then evaporated onto SiO$_2$ in vacuo and the impregnated solid flash chromatographed on 60 g of SiO$_2$ (230–400 mesh) eluted with 1.5 L of 7% CH$_3$—CHCl$_3$ followed by 1 L of 10% CH$_3$OH—CHCl$_3$. Fractions containing the product were pooled and concentrated to give 72 mg of a glassy solid (47% yield).

$^1$H NMR (90 MHz, dmso-d$_6$) δ: 1.1–1.8 (m, 6H); 2.04 (bt, J=7 Hz, 2H); 2.5 (s, 6H); 2.56 (m, 1H); 2.74 (bd, J=4 Hz, 1H); 2.8–3.4 (m, 14H); 3.40 (m, 14H); 4.14 (m, 1H); 4.25 (m, 1H); 4.40 (bd, J=6 Hz, 2H); 6.15 (m, 1H); 6.35 (s, 1H); 7.02 (s, 1H); 7.45 (d, J=8 Hz, 1H); 7.62 (d, J=8 Hz, 1H); 7.80 (m, 1H).

$^{13}$C NMR (22.5 MHz, dmso-d$_6$) δ: 11.9, 18.9, 25.3, 28.2, 28.3, 33.4, 35.2, 55.4, 59.2, 61.0, 69.2, 69.6, 69.8, 70.0, 89.0, 107.8, 112.0, 113.1, 114.3, 120.6, 121.6, 153.6, 154.4, 155.6, 157.9, 159.5, 162.7, 172.1.

EXAMPLE 2B

Large Scale Preparation

A solution containing 760 mg of amino-Peg-biotin (1.5 mmol) and 2 mL of DMF under an argon atmosphere was treated with 292 mg of N,N-carbonyldiimidazole (1.8 mmol). The resulting solution was stirred for 4 hours at room temperature. Analytical TLC (SiO$_2$, 4:1 CHCl$_3$—CH$_3$OH) indicated a complete conversion of starting material (Rf=0.1) to imidazourea (Rf=0.5). The solution was then treated with 243 mg of 4'-aminomethyl-4,5'-dimethylangelicin (1 mmol) and 1.39 mL of diisopropylethylmine (1.03 g, 8 mmol). The resulting mixture was then stirred at 50° C. under an argon atmosphere overnight. The solvents were removed in vacuo. The residue was then dissolved in CH$_3$OH and adsorbed on to SiO$_2$, which was then placed atop a 100 g of SiO$_2$—60 column (230–400 mesh) which had been packed and equilibrated with a 9:1 CHCl$_3$—CH$_3$OH solvent mixture. The column was then flash eluted with this solvent mixture with 25 mL fractions collected. Fractions containing the product were then pooled and concentrated to give 0.63 g of an oil. The product was dissolved in acetone containing a trace of methanol and precipitated with ether. Centrifugation was used to isolate the flocculant white precipitate. The product was dried at 53° C., 0.1 mm, to give 450 mg of a white, tacky solid (52% yield). mp 80°–83° C.

Analysis calculated for C$_{37}$H$_{53}$N$_5$O$_{11}$S: C, 57.11; H, 6.91; N, 9.06, Found: C, 56.61; H, 7.04; N, 9.18.

IR (KBr) cm$^{-1}$: 2910, 2860, 1700, 1635, 1550, 1440, 1375, 1275, 1240, 1100.

The $^1$H NMR spectrum agreed with that of the previously prepared sample.

EXAMPLE 3

N,N'-Dicyanoethyl-N,N'-1,4-Diaminobutane

A solution of 18.64 g of N,N'-dimethyl-1,4-diaminobutane (0.161 mole) was cooled to 0° C. and treated with 23 mL of freshly distilled acrylonitrile (18.54 g, 0.35 mole) added dropwise over 0.5 hours. A mild exotherm was noted during this addition. The resulting mixture was as allowed to cool to ambient temperature over a 1.5 hour period. The mixture was then concentrated in vacuo to remove acrylonitrile at 12 mm and was then distilled at 0.1 mm. Fractions distilling at 207°–222° C. were pooled to yield 30.55 g of product as a colorless oil (85.6% yield).

Analysis: Calculated for C$_{12}$H$_{22}$N$_4$: C, 64.82; H, 9.98; N, 25.20; Found: C, 64.55; H, 10.12; N, 24.84.

$^1$H NMR (60 MHz, CDCl$_3$) δ: 1.45 (m, 4H); 1.92 (s, 6H, —N—CH$_3$); 2.4–3 (m, 12H)

$^{13}$C NMR (22.5 MHz, COCl$_3$) δ: 15.9, 24.7, 41.4, 52.5, 56.6, 118.8 ppm.

IR (CHCl$_3$) cm$^{-1}$: 2950, 2850, 2810, 2250, 1510.

Mass Spectrum: (EI) m/e: 222.2 (M$^+$, 11.9%); 223.3 (M+1, 2.6%).

EXAMPLE 4

N-4, N-9-Dimethylspermine

A solution containing 6.2 g of N,N'-Dicyanoethyl-N,N'-dimethyl-1,4-diaminobutane (28 mmol) in 200 mL of CH$_3$OH was saturated with gaseous ammonia. The solution was then treated with several spatulas full of freshly washed (10X with H$_2$O) Raney Nickel. The mixture was then hydrogenated at 50°–70° C. and 50 psig of H$_2$ in a Paar shaker apparatus. The theoretical amount of H$_2$ was taken-up in 2 hours, but hydrogenation was continued overnight. The mixture was then filtered through Celite and the precipitate washed with CH$_3$OH and H$_2$O. The filtrate was concentrated in vacuo to give 6.48 g of an oily residue. Evaporative distillation at 100°–110° C., 0.05 mm, gave 6.272 g of the product as a colorless oil (97%).

Analysis: Calculated for C$_{12}$H$_{30}$N$_4$: C, 62.56; H, 13.13; N, 24.32; Found: C, 62.43; H, 13.20; N, 24.03.

$^1$H NMR (90 MHz, CDCl$_3$) δ: 1.1 (s, 4H, NH$_2$); 1.3 (m, 4H, C$_6$—, C$_7$—CH$_2$); 1.4 (quintet, 4H, J=7 Hz, C$_2$—, C$_{11}$—CH$_2$); 2.0 (s, 6H, N$_4$—, N$_9$—CH$_3$); 2.15 (m, 8H, C$_3$—, C$_5$—, C$_8$—, C$_{10}$—, CH$_2$); 2.65 (t, J=7 Hz, 4H, C$_1$, C$_{12}$—CH$_2$).

IR (CHCl$_3$) cm$^{-1}$: 3500–3050, 3380, 2920, 2840, 2780, 2500, 1580, 1470.

Upon standing at room temperature several days, a white precipitate resulted which was determined to be the carbonate salt on the basis of the following data:

Analysis: Calculated for C$_{12}$H$_{30}$N$_4$.HCO$_2$: C, 59.73; H, 11.95; N, 21.43; Found: C, 59.84; H, 12.00; N, 22.12.

$^{13}$C NMR (CDCl$_3$) δ: 163.2 ppm.

EXAMPLE 5

N-1-(Biotinylamido)-N-4, N-9-Dimethylspermine

A solution containing 2.907 g of N-4, N-9-dimethylspermine (12.62 mmol) in 25 mL of DMAC (dimethylacetamide) under argon was treated with 1.722 g of N-oxysuccinimidyl biotin (5.05 mmol) added in portions over a 3 hour period. A precipitate was noted one hour after addition. The resulting solution was stirred overnight at ambient temperature. Analytical TLC ($SiO_2$, 15:5:1 $CHCl_3$—$CH_3OH$-concentrated $NH_4OH$, ninhydrin or dimethylaminocinnamaldehyde visualization) indicated the formation of monoacylation product (Rf=0.57). The mixture was filtered and the precipitate washed with DMAC and dried at 55° C., 0.1 mm. This product was identified as the bis-N-oxysuccinimidyl salt of N-4, N-9-dimethylspermine on the basis of the following data. mp: decomposes slowly 96.5°-105° C.

Analysis: Calculated for $C_{20}H_{40}N_6O_6$: C, 52.16; H, 8.75; N, 18.24; Found: C, 52.14; H, 8.33; N, 17.69.

$^1H$ NMR (90 MHz, $D_2O$) δ: 1.55 (m, 4H); 1.86 (q, J=8 Hz, 4H); 2.36 (s, 6H); 2.6 (m, 6H); 2.64 (s, 8H); 2.92 (t, J=8 Hz, 4H).

$^{13}C$ NMR (22.5 MHz, $D_2O$) δ: 22.6, 24.1, 24.7, 37.6, 39.9, 53.1, 55.6, 179.0

IR (KBr) $cm^{-1}$: 3060, 2840, 1760, 1670, 1250, 1100.

The filtrate which contained the desired product was evaporated in vacuo and flash chromatographed on 500 g of $SiO_2$—60 (230-400 mesh) using a 15:5:1 $CHCl_3$—$CH_3OH$—concentrated $NH_4OH$ solvent mixture. Fractions of 25 mL were collected. Fractions containing the product (136-245) were pooled and concentrated to give 1.127 g of a colorless foam, which was precipitated as a white powder from isopropanol-ether and dried at 55° C., 0.1 MM. The yield of product was 958 mg (42%).

Analysis: Calculated for $C_{22}H_{44}N_6O_2S$ $2H_2O$: C, 53.63; H, 9.82; N, 17.06; Found: C, 54.08; H, 9.46; N, 17.25.

$^1H$ NMR (90 MHz, $D_2O$) δ: 1.2-1.9 (m, 14H, $C_6$, $C_7$, $C_{11}$, $C_2$—$H_2$, Bio—$C_\beta$, $C_\gamma$, $C_\delta$—$H_2$), 2.25 (d, 6H, $CH_3$—N—); 2.3-3.0 (m, 12H); 3.2 (t, J=7 Hz, 2H); 3.35 (m, 1H, Bio—$C_2H$), 4.4 (m, 1H, Bio—$C_3H$); 4.6 (m, 1H, Bio—$C_4H$).

$^{13}C$ NMR (22.5 MHz, $D_2O$) δ: 25.8, 27.3, 27.5, 28.9, 29.8, 30.0, 37.7 (Bio—Cδ) 39.6 ($N_4$, $N_9$—$CH_3$); 40.7 (Bio—$C_5$); 41.8 ($C_{12}$); 43.0 ($C_1$); 55.9 (Bio—$C_2$); 57.5 ($C_3$, $C_{10}$); 58.3 ($C_5$, $C_8$); 62.3 (Bio—$C_4$); 64.2 (Bio—$C_3$); 107.3 (Bio—$C_2$); 178.6.

IR (KBr) $cm^{-1}$: 3300, 3100, 2950, 2870, 2810, 1700, 1640, 1550, 1460.

Mass Spectrum: (FAB) m/e: 457 (M+1, 10.4%) 458 (M+2, 3.3%) 459 (M+3, 1.4%)

EXAMPLE 6

Biotinyl-Spermine$^{2+}$-Angelicin

A solution containing 298 mg of N-1 (Biotinylamido)-N-4,N-9-dimethylspermine (0.5 mmol) in 3 mL of DMAC under argon was treated with 97 mg of N,N-carbonyldiimidazole (0.6 mmol). Complete conversion to imidazolide was noted after 4 hours by analytical TLC ($SiO_2$, 15:5:1 $CHCl_3$—$CH_3OH$-concentrated $NH_4OH$, Rf=0.5). The reaction mixture was then treated with 80 mg of 4'-aminomethyl-4,5'-dimethylangelicin (0.33 mmol) and 436 μL of diisopropylethylamine (2.6 mmol). The resulting solution was then stirred at 40° C. overnight. A new product was then noted by analytical TLC ($SiO_2$, 50:10:1 $CHCl_3$—$CH_3OH$-concentrated $NH_4OH$, Rf=0.1). The mixture was then concentrated in vacuo and flash chromatographed on 60 g of $SiO_2$ eluted with a 50:10:1 $CHCl_3$—$CH_3OH$—concentrated $NH_4OH$ solvent mixture. Fractions of 25 mL were collected. Fractions containing the product were pooled and concentrated to a solid, which was dissolved in 5N HCl and evaporated to an oil, which as azeotropically evaporated twice with toluene. The product was then precipitated as a white powder from ethanol-ether and dried at 55° C., 0.1 mm. The yield of product was 209 mg (76%).

Analysis: Calculated for $C_{37}H_{55}N_7O_6S.5H_2O$: C, 50.00; H, 7.37; N, 11.03; Found: C, 50.15; H, 7.65; N, 10.46.

$^1H$ NMR (90 MHz, $D_2O$) δ: 1.1-1.2 (m, 16H); 2.23 (s, 3H, N—$CH_3$); 2.41 (s, 3H, N—$CH_3$); 2.75 (m, 2H); 2.80 (s, 3H, Ang $C_4$—$CH_3$); 2.86 (s, 3H, Ang $C_5'$—$CH_3$); 2.9-3.4 (m, 13H); 4.16 (m, 2H, Ang $C_4'$—$H_2$); 4.35 (m, 1H, Bio $C_3$—H); 4.6 (m, 1H, Bio—$C_4$—H); 6.06 (m, 1H, Ang $C_3$—H); 7.12 (AB quartet, J=8 Hz, 2H, Ang $C_5$—H, $C_6$—H).

CMR (22.5 MHz, $D_2O$) δ: 13.3, 20.6, 22.8, 25.8, 26.3, 27.1, 29.8, 30.1, 36.0, 37.4, 38.2, 38.7, 41.8, 55.6, 57.3, 57.4, 62.4, 64.2, 110.2, 112.4, 113.1, 116.1, 117.6, 122.1, 147.7, 156.6, 157.4, 158.9, 162.0, 165.0, 167.2.

IR (KBr) $cm^{-1}$: 3400, 3260, 2940, 2625, 2500, 1730-1640, 1615, 1560, 1450, 1390, 1285, 1250, 1080.

EXAMPLE 7

4,5'-Dimethyl-4'-Hydroxymethylangelicin

A suspension containing 750 mg of 4'-chloromethyl-4,5'-dimethylangelicin (2.86 mmol) in 500 mL of $H_2O$ was refluxed for 4 hours and then cooled. The precipitate was filtered to give 600 mg of crude product mixture which was flash chromatographed on a 100 g column of $SiO_2$—60 eluted with a 1% $CH_3OH$—$CHCl_3$ solvent mixture. Fractions of 25 mL were collected. Fractions containing the product were pooled and concentrated to give a white solid which has recrystallized from ehtyl acetate and dried at 55° C., 0.1 mm.

Yield = 343 mg (49%). mp 201.5°-203° C. (lit mp 201° C.).

Analysis: Calculated for $C_{14}H_{12}O_4$: C, 68.84; H, 4.95; Found: C, 68.98; H, 4.82.

$^1H$ NMR (90 MHz, dmos-$d_6$) δ: 2.40 (s, 3H); 2.45 (s, 3H); 4.72 (d, J=4 Hz, 2H, —$CH_2$—); 4.9 (t, J=4 Hz, OH); 6.3 (m, 1H); 7.5 (AB quartet, J=9 Hz, $C_5$—H, $C_6$—H).

IR (KBr) $cm^{-1}$: 3430, 3080, 2940, 2900, 1700, 1635, 1620, 1450, 1400, 1380, 1300, 1270, 1090.

Mass Spectrum: EI (m/e): 244.1 ($M^+$, 72.6%); 245.1 (M+1, 12.1%); 198.1 ($M^+$-46, 100%).

EXAMPLE 8

4,5'-Dimethyl-4'-Formylangelicin

A solution containng 175 mg of 4,5'-dimethyl-4'-hydroxymethyl angelicin (0.71 mmol) in 10 mL of $CH_2Cl_2$ was treated with 306 mg of pyridinium chlorochromate (PCC), (0.42 mmol). After 2 hours, an additional 75 mg of PCC was added and the mixture stirred for 1 hour. The mixture was filtered and the precipitate was washed thrice with 5 mL aliquots of $CH_2Cl_2$. The combined organic layers were concentrated and the residue flash chromatographed on 60 g of $SiO_2$—60 (230—400 mesh) eluted with a 0.5% $CH_3OH$—$CHCl_3$ mixture. Fractions of 20 mL were collected. Fractions containing the product were pooled and concentrated to a white solid which was recrystallized from toluene and dried at 55° C., 0.1 mm. The yeild was 79 mg (46%). A second crop of 24 mg (14%) was obtained from concentration of the mother liquor to half volume, precipitation from ether and drying at 55° C., 0.1 mm was conducted. The combined yield was 103 mg (60%). mp 219°-220° C.

Analysis: Calculated for $C_{14}H_{10}O_4$: C, 69.42; H, 4.16; Found: C, 69.44; H, 4.47.

$^1$H NMR (90 MHZ, dmso-$d_6$) δ: 2.57 (s, $C_4$—$CH_3$); 2.90 (s, $C_5'$—$CH_3$); 6.3 (m, $C_3$—H); 7.5 (d, J=8 Hz, $C_5$—H); 7.66 (d, J=8 Hz, $C_6$—H); 10.4 (—CHO).

$^{13}$C NMR (22.5 MHz, dmso-$d_6$) δ: 18.2, 22.8, 112.2, 117.0, 119.9, 120.4, 126.2, 131.8, 158.0, 159.5, 160.9, 163.1, 168.2, 189.8.

IR (KBr) cm$^{-1}$: 3060, 2970, 2860, 1730, 1690, 1615, 1570, 1390, 1070.

Mass Spectrum: EI (m/e): 242.1 ($M^+$, 100%); 243.1 (M+1, 14.9%).

EXAMPLE 9

Biotinyl-Sperrmine$^{3+}$-Angelicin

A suspension of 58 mg of 4'-formyl-4,5'-dimethylangelicin (0.24 mmol) and 137 mg of N-1-(biotinylamido)-N-4,N-9-dimethylspermine (0.3 mmol) in 3 mL of $CH_3OH$ was treated with 25 mg of $NaBH_3CN$ (0.4 mmol). The resulting suspension was warmed briefly to dissolve the contents, and was then stirred two hours at ambient temperature. Analytical TLC ($SiO_2$, 30:10:1 $CHCl_3$—$CH_3OH$-concentrated $NH_4OH$) indicated complete conversion of aldehyde to a mixture containing a major product (Rf=0.3). The mixture was treated with 50 μL of 0.5N HCl and stirred for 5 minutes and was then neutralized with 50 μL of 0.5N NaOH. The solvents were then evaporated in vacuo and the residue flash chromatographed on 60 g of $SiO_2$-60 (230-400 mesh) eluted with a 40:10:1 $CHCl_3$—$CH_3OH$-concentrated $NH_4OH$ solvent mixture. Fractions of 25 mL were collected. Fractions containing the product were pooled and concentrated to an oil which was dissolved in 3 mL of 4N HCl and evaporated to a solid which was azeotropically distilled twice with toluene. The white solid was then precipitated from ethanol-ether and dried at 53° C., 0.1 mm. The yield was 96 mg (51%). mp: effervesced slowly above 147° C., decomposed at 202°-220° C.

Analysis: Calculated for $C_{36}H_{51}Cl_3N_6O_5S$ $6H_2O$: C, 47.92; H, 7.71; N, 9.31; Found: C, 47.91; H, 7.04; N, 9.97.

$^1$H NMR (90 MHz, $D_2O$) δ: 1.1-2.0 (m, 12H), 2.18 (t, J=7 Hz, 4H); 2.35 (s, 3H, N—$CH_3$); 2.48 (s, 3H, N—$CH_3$); 2.8 (m, 2H); 2.79 (s, 3H, Ang $C_4$—$CH_3$); 2.84 (s, 3H, Ang $C_5$—$CH_3$); 2.9-3.5 (m, 13H); 4.3(s, 2H, Ang—$C_4'$—$CH_2$); 4.2-4.4 (m, 2H, Bio $C_3$—H, $C_4$—H); 6.2 (s, 1H, Ang $C_3$—H); 7.36 (d, J=8 Hz, 1H, Ang $C_5$—H); 7.52 (d, J=8 Hz, 1H, Ang $C_6$—H).

$^{13}$C NMR (22.5 MHz, $D_2O$) δ: 13.6, 20.8, 22.9, 25.8, 27.1, 29.8, 30.0, 37.5, 38.0, 41.8, 42.2, 46.1, 54.8, 55.7, 57.1, 62.3, 64.1, 106.4, 110.6, 113.3, 116.7, 117.1, 123.8, 148.1, 158.1, 159.5, 160.6, 165.0, 167.2, 178.2.

IR (KBr) cm$^{-1}$: 3400, 3250, 3050, 2940, 2650, 1720, 1690, 1620, 1450, 1080.

Mass Spectrum: (FAB) m/e: 683 (M+1, 3.5%) 684 (M+2, 1.2%) 685 (M+3, 5.1%)

EXAMPLE 10

Labeling Efficiencies of Three Angelicin Linker Biotin Analogues for DNA Labelling Each of the biotin analogues (products of Examples 2, 6 and 9) were diluted to 10 μM into 0.1M sodium phosphate buffer, pH 7.0, 0.15M NaCl containing 33 μg/mL (50 μM) calf thymus dsDNA. A sample of biotinyl-PEG-angelicin was also diluted into 0.1 mM EDTA, pH 8, with the same amount of DNA. Samples of 50 μL were exposed to light of 340±30 nm for one hour. The samples, along with 50 μL samples not irradiated, were diluted with 450 μL $H_2O$ (0.1M Tris-HCl, pH 8.0, for the samples not containing salt) and extracted 2× with 0.5 mL 2-butanol, diluted 10% v/v with 3M sodium acetate, and the DNA precipitated with two volumes of 100% ethanol. The centrifuged pellets were dried, then dissolved in 250 μL 10 mM Tris-HCl, pH 7.4, 1 mM EDTA. The DNA and biotin concentrations were determined by the method as described in the previous example.

The folllwing results clearly show that the spermine linkers are superior to PEG linker:

| Product of example | Compound | Base Pairs DNA/Biotin | |
|---|---|---|---|
| | | Non-Irradiated | Irradiated |
| 2 | Biotinyl-PEG-angelicin | 0 | 154 |
| — | (No Salt) | 5100 | 80 |
| 6 | Biotinyl-spermine$^{+2}$-angelicin | 0 | 15 |
| 9 | Biotinyl-spermine$^{+3}$-angelicin | 625 | 32 |

EXAMPLE 11

Efficiency of Whole Cell Lysate Labeling of Different Compounds

For each labelling reaction approximately $10^8$ E. Coli cells were taken in 1 borate buffer (10 mM pH 8.2). To the suspension 0.1 ml 1 (N) sodium hydroxide solution was added. The mixture was then heated in a boiling water bath to lyse the cells for 10 minutes. The lysed cells were then neutralized by HCl solution in ice. After the neutralization, 50 μg of labelling reagent dissolved in water (approximately 1 mg/ml) was added. The mixture was then irradiated for 60 minutes using a long wavelength setting of UVL 56 (UV Products, Inc., San Gabriel, California, U.S.A.) hand held lamp (for furocoumarines) or a "KODAK" projector lamp (ELH 120 v 300 w) (for azido photobiotin or Forster's compound). For two step labelling, an overnight incubation with N-hydroxysuccinimidobiotin was done after the photoreaction. No purification was carried out after any of these reactions. A two step process for whole cell lysate produces non-specific biotinylated products, e.g., proteins.

The labelled cells were then spotted onto nitrocellulose paper in equivalent amounts of $10^5$, $10^4$, $10^3$, $10^2$, $10^1$, and 0 cell number; 5, 4, 3, 2, 1 and 0 are respective amounts on the filter. In the figure, the letters f, Si, bp, b* and B respectively represent Forster's photobiotin (Nucleic Acids Res., 13(3), 745, (1985)) spermine linked angelicin (Example 9) PEG linked angelicin (Example 2) two step labelling and blank as the photolabelling reagents.

The chemiluminescent detection of label was done as follows:

The nitrocellulose strip containing the biotinylated cell lysate was incubated in a solution (approximately 3 ml) containing 250 μg/ml avidin linked horseradish peroxidase 0.1M tris (pH 7.5); 0.1M NaCl; 2 mM MgCl$_2$, 0.05% Triton×100 and 20 μg/ml calf thymus DNA for 30 minutes at room temperature. The strip was then washed twice with the same buffer without the avidin linked horseradish peroxidase and calf thymus DNA. Then it was placed in a petri dish containing 5 ml 60 μM iodophenol in 40 mM tris and 40 mM ammonium acetate (pH 8.2) mixture. Then 1:1 v/v (10 ml) luminol: H$_2$O$_2$ (1 mM:2.5 mM final) was added and the emitted light was recorded by exposing a "POLAROID" film (type 57) in a dark room. The results clearly indicate that spermine linked angelicin is superior to PEG linked angelicin in its labelling efficiency. Conclusion: With pure DNA or with cell lysate nucleic acids polyamine linkers show superior labelling property than the corresponding PEG linkers.

It will be appreciated that the instant specification and claims are set forth by way of illustration and not limitation, and that various modifications and changes may be made without departure from the spirit and scope of the present invention.

What is claimed is:

1. A photochemical nucleic acid-labeling reagent of the formula

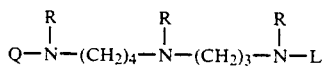

wherein Q is a photoreactive residue of a nucleic acid-binding ligand; L is a detectable label residue; R is hydrogen, C$_1$ to C$_7$-alkyl, aryl, hydroxy, or C$_1$ to C$_7$-alkoxy; wherein R can be the same or different each time R appears in the formula.

2. A reagent according to claim 1, wherein R is hydrogen or C$_1$ to C$_4$-alkyl.

3. A reagent according to claim 1, wherein the photoreactive residue of a nucleic acid-binding ligand is a photoreactive residue of an intercalator compound.

4. A reagent according to claim 3, wherein the intercalator compound is selected from the group consisting of acridine dyes, phenanthridines, phenazines, furocoumarins, phenothiazines, quinolines and antracyclines.

5. A reagent according to claim 4, wherein the intercalator compound is selected from the group consisting of furocoumarins and phenanthridines.

6. A reagent according to claim 3, wherein the intercalator compound is of the formula

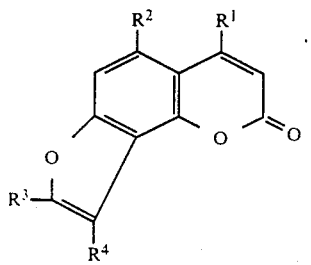

in which R$^1$, R$^2$ and R$^3$ each independently is hydrogen or C$_1$-C$_7$-alkyl; and R$^4$ is hydrogen, C$_1$-C$_7$-alkyl or C$_1$-C$_7$-alkyl substituted with hydroxy, C$_1$-C$_7$-alkoxy, amino, halo, or is of the formula

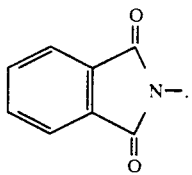

7. A reagent according to claim 3, wherein the intercalator compound is 4'-aminomethyl-4,5'-dimethylangelicin.

8. A reagent according to claim 3, wherein the intercalator compound is of the formula

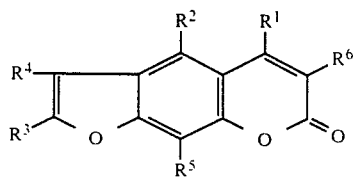

in which R$^1$, R$^3$ and R$^6$ each independently is hydrogen or C$_1$-C$_7$-alkyl; R$^4$ is hydrogen, C$_1$-C$_7$-alkyl or C$_1$-C$_7$-alkyl substituted with hydroxy, C$_1$-C$_7$-alkoxy, amino, halo, or is of the formula

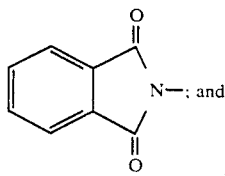

R$^2$ and R$^5$ each independently is hydrogen, hydroxy, carboxy, carbo-C$_1$-C$_7$-alkoxy or C$_1$-C$_7$-alkoxy.

9. A reagent according to claim 3, wherein the intercalator compound is 4'-aminomethyl-4,5',8-trimethylpsoralen.

10. A reagent according to claim 1, wherein the detectable label residue is a residue of a moiety selected from the group consisting of biotin, a hapten, an enzyme, a fluorescent molecule and a luminescent molecule.

11. A reagent according to claim 1, wherein the detectable label residue is selected from the group consisting of a biotin and a hapten residue.

12. A labeled nucleic acid comprising (a) a nucleic acid component, (b) a nucleic acid-binding ligand photochemically linked to the nucleic acid component, (c) a label, and (d) a spacer chemically linking (b) and (c) and being of the formula

wherein R is hydrogen, C$_1$-C$_7$ alkyl, aryl, hydroxy, or C$_1$-C$_7$ alkoxy; wherein R can be the same or different each time R appears in the formula.

13. A labeled nucleic acid according to claim 12, wherein R is hydrogen or C$_1$-C$_4$ alkyl.

14. A labeled nucleic acid according to claim 12, wherein the nucleic acid-binding ligand is an intercalator compound.

15. A labeled nucleic acid according to claim 14, wherein the intercalator compound is selected from the group consisting of acridine dyes, phenanthridines, phenazines, furocoumarins, phenothiazines, quinolines and anthracyclines.

16. A labeled nucleic acid according to claim 15, wherein the intercalator compound is selected from the group consisting of furocoumarins and phenanthridines.

17. A labeled nucleic acid according to claim 14, wherein the intercalator compound is of the formula

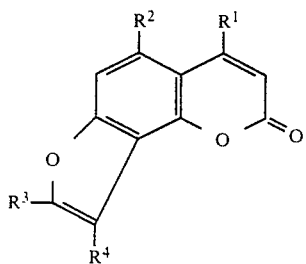

in which $R^1$, $R^2$ and $R^3$ each independently is hydrogen or lower alkyl; and $R^4$ is hydrogen, $C_1$-$C_7$-alkyl or $C_1$-$C_7$-alkyl substituted with hydroxy, $C_1$-$C_7$-alkoxy, amino, halo, or is of the formula

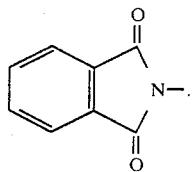

18. A labeled nucleic acid according to claim 14, wherein the intercalator compound is 4'-aminomethyl-4,5'-dimethylangelicin.

19. A labeled nucleic acid according to claim 14, wherein the intercalator compound is of the formula

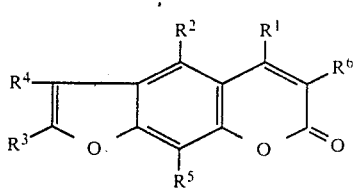

in which $R^1$, $R^3$ and $R^6$ each independently is hydrogen or $C_1$-$C_7$-alkyl; $R^4$ is hydrogen, $C_1$-$C_7$-alkyl or $C_1$-$C_7$-alkyl substituted with hydroxy, $C_1$-$C_7$-alkoxy, amino, halo, or is of the formula

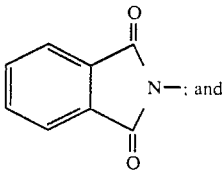

$R^2$ and $R^5$ each independently is hydrogen, hydroxy, carboxy, carbo-$C_1$-$C_7$-alkoxy or $C_1$-$C_7$-alkoxy.

20. A labeled nucleic acid according to claim 14, wherein the intercalator compound is 4'-aminomethyl-4,5'-8-trimethylpsoralen.

21. A labeled nucleic acid according to claim 12, wherein the label is selected from the group consisting of biotin, a hapten, an enzyme, a fluorescent molecule and a luminescent molecule.

22. A labeled nucleic acid according to claim 12, wherein the label is selected from the group consisting of biotin and a hapten.

23. A labeled nucleic acid according to claim 12, wherein the nucleic acid component is DNA.

24. A labeled nucleic acid according to claim 12, wherein the nucleic acid component is RNA.

25. A labeled nucleic acid according to claim 12, wherein the nucleic acid component is an oligonucleotide.

* * * * *